United States Patent
Pellens et al.

(10) Patent No.: US 9,085,515 B2
(45) Date of Patent: Jul. 21, 2015

(54) CONTINUOUS PROCESS TO MAKE AMINE OXIDE

(71) Applicant: The Proctor & Gamble Company, Cincinnati, OH (US)

(72) Inventors: Linda Pellens, Erps-Kwerps (BE); Christopher Stephen Jones, Saint-Gilles (BE); Rasim Tanbug, West Chester, OH (US); Walter Agnes Louis Nuyts, Mechelen (BE); Diederik Emiel Omer Vanhoutte, Deinz (BE); Joey Jay Schriner, Shawnee, KS (US)

(73) Assignee: The Procter & Gamble Company, Cincinnati, OH (US)

( * ) Notice: Subject to any disclaimer, the term of this patent is extended or adjusted under 35 U.S.C. 154(b) by 114 days.

(21) Appl. No.: 13/949,275

(22) Filed: Jul. 24, 2013

(65) Prior Publication Data

US 2014/0031591 A1    Jan. 30, 2014

Related U.S. Application Data

(60) Provisional application No. 61/674,977, filed on Jul. 24, 2012.

(51) Int. Cl.
*C07C 291/00* (2006.01)
*C07C 291/04* (2006.01)

(52) U.S. Cl.
CPC .................................... *C07C 291/04* (2013.01)

(58) Field of Classification Search
CPC ........................... C07C 291/04; C07C 291/02
See application file for complete search history.

(56) References Cited

U.S. PATENT DOCUMENTS

| 4,970,340 A | 11/1990 | Smith |
| 5,710,333 A | 1/1998 | Bäder et al. |
| 6,037,497 A | 3/2000 | Thomas et al. |
| 6,166,255 A | 12/2000 | Cochran et al. |
| 2002/0095055 A1* | 7/2002 | Choudary et al. ............ 564/298 |
| 2003/0078424 A1* | 4/2003 | Wurziger et al. ................ 546/1 |

OTHER PUBLICATIONS

International Search Report; International Application No. PCT/US2013/049657; date of mailing Oct. 10, 2013; 10 pages.

* cited by examiner

*Primary Examiner* — Rosalynd Keys
*Assistant Examiner* — Jennifer C Sawyer
(74) *Attorney, Agent, or Firm* — John T. Dipre; Steven W. Miller

(57) ABSTRACT

A continuous process for making amine oxide surfactant comprising the steps of (a) providing the following components; a tertiary amine composition and an aqueous hydrogen peroxide composition, (b) mixing the components from step a) in a mixing device, (c) passing the mixture exiting the mixing device from step b) into an aqueous amine oxide composition comprising from 65 to 80 wt % amine oxide, (d) adjusting the temperature of the amine oxide composition made in step c) to between 40 and 80° C., (e) collecting the amine oxide surfactant; and wherein, for every 1 part of the component mixture from step b) being passed into the aqueous stream in step c), between 8 and 30 parts of the temperature adjusted amine oxide composition from step d) are recycled back to step b) and passed through the mixing device together with the components from step a).

16 Claims, No Drawings

CONTINUOUS PROCESS TO MAKE AMINE OXIDE

FIELD OF THE INVENTION

The present invention contemplates a process for making amine oxide.

BACKGROUND OF THE INVENTION

Amine oxides are used in many commercial products, such as laundry detergents, fabric softeners, and shampoos. They provide benefits such as softness, hand mildness and suds generation.

Traditional techniques for making amine oxide have utilized batch processes and result in aqueous compositions comprising approximately 30% by weight of the aqueous composition of amine oxide. Thus, in order to achieve required levels of amine oxide in final commercial products, large quantities of aqueous amine oxide compositions need to be added.

The addition of large quantities of these aqueous amine oxide compositions results in the addition of large quantities of water. This has the negative effect of reducing the formulation freedom of the final commercial product due to the presence of the water. Furthermore, the presence of large quantities of water in the aqueous amine oxide composition results in transportation inefficiency since large quantities of water need to be transported resulting in increased costs.

It is desirable to develop a process to manufacture amine oxide compositions comprising at least 65% by weight of amine oxide. However, there is a general reluctance in the field to achieve this due to the very long reaction times needed to make amine oxide compositions. Commercial scale batch processes used today to make 30% by weight amine oxide compositions can take up to 8 hours to complete. Thus the expectation is that it would take even longer to manufacture an at least 65% amine oxide composition. Furthermore, the amine oxide present in a composition comprising at least 65% by weight amine oxide would mostly exist in the lamellar phase. To arrive at the lamellar phase, the amine oxide composition would firstly need to pass through the hexaganol phase which results in highly viscous amine oxide compositions. This is very difficult to handle during manufacture.

Thus there is a need in the art for a process capable of producing an amine oxide composition comprising concentrations of at least 65% amine oxide so minimizing the amount of water present. It is also desirable to develop a continuous process in which at least 65 wt % amine oxide compositions can be efficiently and quickly produced.

It was surprisingly found that the process of the present invention solved the above mentioned problems.

SUMMARY OF THE INVENTION

A continuous process for making amine oxide, comprising the steps of:
  a) Providing the following components; a tertiary amine composition and an aqueous hydrogen peroxide composition;
  b) mixing the components from step a) in a mixing device;
  c) passing the mixture exiting the mixing device from step b) into a pre-prepared aqueous amine oxide composition comprising from 65 to 80wt % amine oxide;
  d) adjusting the temperature of the amine oxide composition made in step c) to between 40 and 80° C.;
  e) collecting the amine oxide surfactant; and
wherein, for every 1 part of the component mixture from step b) being passed into the pre-prepared amine oxide composition in step c), between 8 and 30 parts of the temperature adjusted amine oxide composition from step d) are recycled back to step b) and passed through the mixing device together with the components from step a).

DETAILED DESCRIPTION OF THE INVENTION

Process

The present invention is to a continuous process for making amine oxide surfactant comprising the steps of:
  a) Providing the following components; a tertiary amine composition and an aqueous hydrogen peroxide composition;
  b) mixing the components from step a) in a mixing device;
  c) passing the mixture exiting the mixing device from step b) into an aqueous amine oxide composition comprising from 65 to 80 wt % amine oxide;
  d) adjusting the temperature of the amine oxide composition made in step c) to between 40 and 80° C.;
  e) collecting the amine oxide surfactant; and
wherein, for every 1 part of the component mixture from step b) being passed into the aqueous stream in step c), between 8 and 30 parts of the temperature adjusted amine oxide composition from step d) are recycled back to step b) and passed through the mixing device together with the components from step a).

Without wishing to be bound by theory, it is believed that although it is possible to make an amine oxide composition comprising at least 65 wt % amine oxide using a batch process, it would not be possible to achieve this on an industrial scale. This is due to the high viscosity experienced when passing through the hexaganol phase. The energy input required for the mixer to mix the composition would be extremely high. However, using the continuous process of the present invention, it is possible to continually make at least 65 wt % amine oxide compositions without suffering from the high energy requirements of a batch process. Furthermore, batch processes tend to incorporate gas bubbles into compositions. Thus, following the batch production, there is often required a 'settling time' in order to 'de-aerate' the compositions. Such aeration is not seen using continuous processes.

Typically, amine oxide surfactants herein are produced by oxidizing the desired tertiary amine with hydrogen peroxide. The present invention is to a continuous process for production of amine oxide. The process comprises the addition of fresh components required to make amine oxide surfactant via a mixing device into a pre-prepared amine oxide composition comprising between 65 wt % and 80 wt % or even 63 wt % and 80 wt % or even 65 wt % and 78 wt %, or even 70 wt % and 75 wt % or even 65 wt % and 75 wt % amine oxide. For every 1 part of fresh components added, between 8 and 30 parts, or even 10 and 30 parts of the amine oxide composition are recycled back to the mixing device. Hence pre-prepared amine oxide is mixed with fresh components and then passed into the amine oxide composition. Concurrently, for every 1 part of fresh components added, 1 part of final amine oxide composition is collected.

Preferably, the process is conducted at a pH of between 7 and 10, preferably between 8 and 10. Without being bound by theory it is believed that this pH is advantageous as at higher pH the amine oxide produced will decompose. At a pH below this range, the amine oxide will complex with hydrogen. Those skilled in the art will recognize standard techniques to measure the pH of the composition.

Preferably, the process comprises essentially no solvent except for water. By 'essentially no solvent' we herein mean no deliberately added solvent except for water. Therefore, minor levels of solvent present in raw materials can be present. In one aspect, there is no solvent present apart for water.

Step a): The following components are provided; a tertiary amine composition and an aqueous hydrogen peroxide composition. The tertiary amine composition and the aqueous hydrogen peroxide compositions are described in more detail below.

A catalyst may also be provided as a further component. The catalyst increases the rate of reaction of the tertiary amine and hydrogen peroxide, without itself undergoing any permanent chemical change. The catalyst is described in more detail below.

A chelant may be provided as yet a further component. The chelant is described in more detail below.

Step b): The components from step a) are mixed in a mixing device. The components may be passed into the mixing device as separate individual streams, or as a plurality of separate streams comprising two or more of the components. Or, the component may be pre-mixed in for example a large tank, prior to being fed into the mixing device as a single stream. Typically, the components are passed into the mixer via pipes or channels. Those skilled in the art will be able to identify suitable pipes or channels for this purpose, and suitable materials for construction of said pipes or channels.

The mixing device can be any mixing device suitable for mixing liquid components. The mixing device may be a high shear mixing device. The high shear mixing device may have an Energy Dissipation rate of at least 1000 W/kg. The high shear mixing device may have an Energy Dissipation rate of up to 100,000,000 W/kg, or even 1,000,000 W/kg. The high shear mixing device may have an Energy Dissipation rate of between 10,000 and 100,000 W/kg. The high shear mixing device can be selected from the group comprising micro-channel mixing devices, static mixers, dynamic mixers and liquid whistle devices. It may be preferred that the mixing device is a dynamic mixer, or even a high shear dynamic mixer.

Without wishing to be bound by theory, it is believed that a high shear mixer is advantageous as it tends to avoid high pressure drops within the production apparatus. Furthermore, the high shear mixing device is less prone to clogging.

Step c): The mixture exiting the mixing device in step b) is passed into a pre-prepared aqueous amine oxide composition comprising from 65 to 80 wt % amine oxide. Without wishing to be bound by theory, the amine oxide present in the aqueous amine oxide composition at a concentration of 65 to 80 wt % is in the lamellar phase. As the concentration of amine oxide increases, it passes through a number of different phases, including the highly viscous hexagonal phase. However, the components from step a) will produce fresh amine oxide as they react in the aqueous amine oxide composition in step c) but will produce lamellar phase amine oxide straightaway without first going through hexagonal phase. It is believed this is due to the dilution effect of the predominately lamellar phase amine oxide present in the pre-prepared amine oxide composition. Hence no significant increase in viscosity is seen. The pre-prepared amine oxide composition is described in more detail below.

It is understood that the pre-prepared aqueous amine oxide composition has been previously made by reacting a tertiary amine composition and aqueous hydrogen peroxide composition. Typically, the tertiary amine composition and the aqueous hydrogen peroxide composition used are the same as the components provided in step a).

Typically, the mixture exiting the mixing device in step b) is passed into the pre-prepared aqueous amine oxide composition through a pipe or channel. The pre-prepared aqueous amine oxide composition may be in a separate pipe, or even in a tank or other storage vessel. Those skilled in the art will be able to identify suitable pipes, channels, tanks and the like for this purpose, and suitable materials for construction of said pipes, channels, tanks or the like.

The aqueous amine oxide composition, which comprises both pre-prepared amine oxide and fresh components may be passed through one or more pumps. The pumps may be low or high pressure pumps, and may for example be used to increase flow rate of the composition.

Step d): The aqueous amine oxide composition that comprises both the pre-prepared amine oxide and also the fresh ingredients made in step c) is adjusted to a temperature of between 40 and 80° C. The temperature may be adjusted to between 30 and 80° C., or even 37 and 80° C. or even 30 and 70° C. or even 35 and 65° C.

The temperature of the amine oxide composition may be adjusted by passing the composition through a suitable device that is capable of raising, lowering or maintaining the temperature. The temperature of the amine oxide composition may be adjusted by passing the composition through a heat exchanger device, or through more than one heat exchanger device, the devices being positioned in series to one another. The heat exchanger devices can be independently selected from the group comprising micro-channel heat exchanger device, plate and frame heat exchanger and shell and tube heat exchangers, preferably plate and frame heat exchanger. Alternatively, the temperature of the amine oxide composition may be adjusted by passing the amine oxide through a heated pipe or the like. The pipe may be heated by a heating jacket, or an electrical heating source or the like.

For every 1 part of the component mixture from step b) being passed into the aqueous pre-prepared amine oxide in step c), between 8 and 30 parts, or even between 10 and 30 parts or even between 10 and 15 parts of the temperature adjusted aqueous amine oxide composition from step d) are recycled back to step b) and passed through the mixing device together with the components from step a). Without wishing to be bound by theory, it is believed that this recycling step ensures sufficient reaction of the tertiary amine with the hydrogen peroxide to produce 65 to 80 wt % amine oxide compositions. The recycle stream acts as a 'phase buffer' to keep the amine oxide in the lamellar phase so that new amine oxide being produced in the apparatus is also in the lamellar phase. Furthermore, the recycle step acts as a heat sink for the heat of reaction, so avoiding high temperature increases.

Typically, the aqueous amine oxide composition is recycled to the mixing device via a pipe or channel. Those skilled in the art will be able to identify suitable pipes or channels for this purpose, and suitable materials for construction of said pipes or channels.

Step e): The amine oxide surfactant is collected. For every 1 part of fresh components added in step a), 1 part of amine oxide surfactant is collected. The collected amine oxide surfactant may be cooled to a temperature between 20 and 50° C., preferably between 30 and 40° C. The residence time can be up to 8 hours, or even up to 6 hours. The residence time may be from 40 to 200 minutes, or even from 60 to 150 minutes. By residence time we herein mean the average time a particle spends within the apparatus used to perform the methods of the present invention.

Tertiary Amine

The continuous process comprises a reaction between a tertiary amine and an aqueous hydrogen peroxide composition. The tertiary amine can have the general formula;

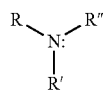

wherein R' and R" are independently selected from C1-C4 alkyl or hydroxyalkyl group, preferably a methyl group; and R is selected from C8-C18 linear, branched, cyclic alkyl or alkenyl groups, preferably, R is selected from C10-C18 linear, branched, cyclic alkyl or alkenyl group, most preferably R is selected from C12-C16 linear, branched, cyclic alkyl or alkenyl group.

In a preferred embodiment, the tertiary amine is alkyldimethylamine.

Aqueous Hydrogen Peroxide Composition

The oxidation step herein is conducted using hydrogen peroxide or a source of hydrogen peroxide, or hydrogen peroxide generated in situ. The oxidation is conducted in water. Hydrogen peroxide is commercially available in aqueous solutions of various strengths up to 90%, which makes it a convenient oxidizing agent for forming amine oxide solutions at the desired concentration.

Catalyst

If present, the catalyst is selected from the group comprising alkali metal bicarbonates, alkali-earth metal bicarbonates, ammonium bicarbonate and mixtures thereof, preferably ammonium bicarbonate or sodium bicarbonate or mixtures thereof, most preferably sodium bicarbonate. The catalyst may be present at a concentration of 0.3 to 2.5% by weight of the tertiary amine.

Chelant

If present, the chelant is preferably a phosphonate-based chelant. Such preferred phosphonate-based chelants are available commercially as Dequest-2066 from manufacturer Thermphos. The chelant may be present at a concentration of at least 5 ppm, or even at least 10 ppm, or even at least 15 ppm. The chelant may be present at a concentration of at most 100 ppm, or even at most 80 ppm, or even at most 50 ppm, or even at most 40 ppm.

Pre-Prepared Amine Oxide Composition

In order for the process to run continuously, a pre-prepared amine oxide composition needs to firstly be prepared. Once an initial pre-prepared amine oxide has been made, the process can then run continuously following the steps detailed above. The pre-prepared amine oxide composition can be an aqueous composition. The pre-prepared amine oxide composition can comprise between 65 wt % and 80 wt % or even 63 wt % and 80 wt % or even 65 wt % and 78 wt %, or even 70 wt % and 75 wt % or even 65 wt % and 75 wt % amine oxide. Preferably, the pre-prepared amine oxide is made from the same tertiary amine as the amine oxide composition described above.

The pre-prepared amine oxide can be prepared using the same process as detailed above, or can be made using a different process, for example a batch process. If the pre-prepared amine oxide is made using the process of the present invention then the process may also comprise a solvent in order to dilute the amine oxide produced. This is advantageous so that as the amine oxide concentration increases the increased viscosity due to the amine oxide being predominantly in the hexagonal phase does not cause a blockage of the apparatus. The solvent stream can be discontinued once a particular level of amine oxide is produced. Thus, once the continuous process is running, then there is essentially no, preferably no solvent present apart from water.

Once the pre-prepared amine oxide composition has been made for the first time, then new ingredients can be mixed following the process according to the present invention, and the process can be run continuously.

The solvent can be any solvent. In one embodiment the solvent is ethanol.

Amine Oxide Surfactant

The amine oxide surfactant is collected continuously. For every 1 part of components added in step a), 1 part of amine oxide surfactant is collected in step e). The amine oxide surfactant can then be stored or formulated into a consumer product. Suitable consumer products include hand dish compositions, automatic dish washing compositions, hard surface cleaners, fabric cleaning compositions and the like.

EXAMPLES

Amine oxide compositions were prepared using processes according to the present invention and using a batch process outside of the scope of the present invention.

Process 1 was according to the present invention. A composition was prepared by mixing tertiary amine, chelant, catalyst and aqueous hydrogen peroxide in a dynamic high shear mixer. The composition comprised 68.1 wt % tertiary amine, 24 wt % of 50% active hydrogen peroxide in water, 0.41 wt % of 25% active chelant in water and 0.66% sodium bicarbonate catalyst. The tertiary amine composition comprising a blend of C12 and C14 alkyldimethyl tertiary amines and N,N-Dimethyl alkalimine. The mixture produced was passed into a pre-prepared aqueous amine oxide composition comprising 58 wt % amine oxide. For every 1 part of new material added, 25 parts were recycled back to the mixer at a temperature of between 40 and 50° C.

The apparatus comprised pre-prepared amine oxide composition comprising 58 wt % amine oxide. Greater then 65 wt % amine oxide was collected after 100 min, and was continually collected thereafter.

Process 2 was a batch process. A composition comprising 70 wt % tertiary amine, 21.7% hydrogen peroxide, and the remainder being water and minor catalyst and chelant levels was prepared in a batch tank. The tertiary amine composition comprising 74% by weight of $C_{12}$ alkyldimethyl tertiary amine, 24% by weight of $C_{14}$ alkyldimethyl tertiary amine and 2% by weight of $C_{16}$ alkyldimethyl tertiary amine. The composition was then mixed in a batch mixing tank. As can be seen in Table 1, following 120 mins, only 24.5 wt % amine oxide was collected. After 360 mins, 68.6 wt % amine oxide was collected.

TABLE 1

| Time | wt % Amine oxide |
|---|---|
| 0 | 0 |
| 60 | 12.6 |
| 120 | 24.5 |
| 180 | 33.6 |
| 240 | 43.4 |
| 300 | 56 |
| 360 | 68.6 |

As can be seen from above, it took only 100 mins to produce 65 wt % amine oxide compositions using the process of the present invention. However, using a traditional batch process, it took 360 mins to achieve the same result. High concentration amine oxide compositions were produced quickly and efficiently using the process of the present invention. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A continuous process for making amine oxide, comprising the steps of;
   a) providing the following components; a tertiary amine composition and an aqueous hydrogen peroxide composition;
   b) mixing the components from step a) in a mixing device;
   c) passing the mixture exiting the mixing device from step b) into a pre-prepared aqueous amine oxide composition comprising from about 65 to about 80 wt % amine oxide;
   d) adjusting the temperature of the amine oxide composition made in step c) to between about 40 and about 80° C.;
   e) collecting the amine oxide surfactant; and
   wherein, for every 1 part of the component mixture from step b) being passed into the pre-prepared amine oxide composition in step c), between about 8 and about 30 parts of the temperature adjusted amine oxide composition from step d) are recycled back to step b) and passed through the mixing device together with the components from step a).

2. The continuous process according to claim 1, wherein for every 1 part of the component mixture from step b) being passed into the pre-prepared amine oxide composition in step c), between about 10 and about 30 parts of the temperature adjusted stream from step d) are recycled back to step b).

3. The continuous process according to claim 1, wherein the mixing device is a high shear mixing device having an Energy Dissipation rate of at least about 1000 W/kg.

4. The continuous process according to claim 3, wherein the high shear mixing device is selected from the group comprising micro-channel mixing devices, static mixers, dynamic mixers and liquid whistle devices.

5. The continuous process according to claim 1, wherein the amine oxide composition in step e) is cooled to a temperature between about 20 and about 50° C., or even between about 30 and about 40° C.

6. The continuous process according to claim 1, wherein the tertiary amine has the general formula:

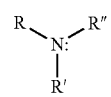

wherein R' and R" are independently selected from C1-C4 alkyl or hydroxyalkyl group; and
R is selected from C8-C18 linear, branched, cyclic alkyl or alkenyl groups.

7. The continuous process according to claim 6, wherein R is selected from C10-C18 linear, branched, cyclic alkyl or alkenyl group.

8. The continuous process according to claim 7, wherein R is selected from C12-C16 linear, branched, cyclic alkyl or alkenyl group.

9. The continuous process according to claim 8, wherein the tertiary amine is alkyldimethylamine.

10. The continuous process according to claim 1 wherein at least one of process steps a) to e) comprises a chelant.

11. The continuous process according to claim 10, wherein the chelant is a phosphonate-based chelant.

12. The continuous process according to claim 10, wherein the chelant is present at a concentration of at least about 5 ppm and at most about 80 ppm.

13. The continuous process according to claim 1, wherein at least one of process steps a) to e) comprises a catalyst selected from the group comprising alkali metal bicarbonates, alkali-earth metal bicarbonates, ammonium bicarbonate and mixtures thereof.

14. The continuous process according to claim 13, wherein the catalyst is present at between about 0.3 and about 2.5% by weight of the tertiary amine.

15. The continuous process according to claim 1, wherein at least one of process steps a) to e) has a pH between about 7 and about 10.

16. The continuous process according to claim 1 wherein at least one of process steps a) to e) comprises no solvent apart from water.

* * * * *